United States Patent
Honaryar et al.

(10) Patent No.: US 11,187,369 B2
(45) Date of Patent: Nov. 30, 2021

(54) MOVABLE RACK ARM WITH COUNTERBALANCE SPRING FOR CONTOURED NON-LINEAR FORCE TRANSFER

(71) Applicant: Alcon Inc., Fribourg (CH)

(72) Inventors: Babak Honaryar, Orinda, CA (US); Mani Irannejad, Santa Ana, CA (US)

(73) Assignee: Alcon Inc., Fribourg (CH)

( * ) Notice: Subject to any disclaimer, the term of this patent is extended or adjusted under 35 U.S.C. 154(b) by 71 days.

(21) Appl. No.: 16/656,442

(22) Filed: Oct. 17, 2019

(65) Prior Publication Data
US 2020/0191322 A1    Jun. 18, 2020

Related U.S. Application Data

(60) Provisional application No. 62/781,235, filed on Dec. 18, 2018.

(51) Int. Cl.
| | |
|---|---|
| *F16M 11/10* | (2006.01) |
| *F16H 19/04* | (2006.01) |
| *F16H 21/44* | (2006.01) |
| *F16M 11/04* | (2006.01) |
| *F16M 11/18* | (2006.01) |
| *F16M 11/42* | (2006.01) |

(52) U.S. Cl.
CPC ............ *F16M 11/10* (2013.01); *F16H 19/04* (2013.01); *F16H 21/44* (2013.01); *F16M 11/046* (2013.01); *F16M 11/18* (2013.01); *F16M 11/42* (2013.01); *F16M 2200/041* (2013.01); *F16M 2200/063* (2013.01); *F16M 2200/066* (2013.01)

(58) Field of Classification Search
CPC ...... F16M 11/10; F16M 11/046; F16M 11/18; F16M 11/42; F16M 2200/041; F16M 2200/063; F16M 2200/066; F16M 11/2021; F16M 2200/04; F16M 2200/06; F16H 19/04; F16H 21/44; A61B 2090/5025; A61B 2090/504; F61B 2090/506
USPC ...................................... 248/558, 648, 123.2
See application file for complete search history.

(56) References Cited

U.S. PATENT DOCUMENTS

| | | | | |
|---|---|---|---|---|
| 4,726,253 | A * | 2/1988 | Russell | ................. F16F 15/043 16/322 |
| 9,939,603 | B2 | 4/2018 | Vasseur | |
| 2008/0067302 | A1* | 3/2008 | Olivera | .................. F16M 13/00 248/183.1 |
| 2010/0127144 | A1 | 5/2010 | Lange | |
| 2010/0176254 | A1 | 7/2010 | Sweere et al. | |
| 2012/0037785 | A1* | 2/2012 | Xu | ........................ F16M 11/24 248/571 |
| 2012/0291582 | A1 | 11/2012 | Kang et al. | |
| 2017/0082819 | A1* | 3/2017 | Vasseur | ................. F16M 11/04 |

* cited by examiner

*Primary Examiner* — Christopher Garft (57) ABSTRACT

The present disclosure relates to a movable rack arm assembly including a cam housing, a circular gear, a rack arm, a cam, and a spring assembly for contoured non-linear force transfer.

10 Claims, 11 Drawing Sheets

MOVABLE RACK ARM WITH COUNTERBALANCE SPRING FOR CONTOURED NON-LINEAR FORCE TRANSFER

TECHNICAL FIELD

The present disclosure provides a movable rack arm with a counterbalance spring that allows contoured non-linear force transfer with respect to the arm. The present disclosure also provides equipment, such as surgical equipment, particularly ophthalmic surgical equipment containing such a movable rack arm.

BACKGROUND

Movable rack arms often benefit from a counterbalance spring that prevents the arm from moving too easily in a given direction. For example, it is often useful for surgical equipment to be attached to movable rack arms so that it can be manipulated during surgery, for example to be brought into or moved out of a surgical field, or moved with respect to the patient or surgeon. However, it is also often important for the movable rack arm and the attached equipment to move too readily, as the surgery might be disrupted or the patient might suffer an injury. A counterbalance spring is often used to prevent a movable rack arm and attached equipment from moving too easily, for example, in response to an accidental bump.

SUMMARY

The present disclosure relates to a surgical console including a base, a tray or screen assembly, a parallelogram arm, and a movable rack arm assembly attached to the base, the tray or screen assembly, or the parallelogram arm. The movable rack arm assembly includes a cam housing including an internal rack arm guide pin and an axle, a circular gear including circular gear teeth and mounted on and rotatable about the axle, a rack arm, a cam, and a spring assembly. The rack arm includes a rack arm attachment attached to the base, the tray or screen assembly, or the parallelogram arm, a rack gear including rack gear teeth, and a rack arm track associated with the internal rack arm guide pin to hold the rack gear teeth engaged with the circular gear teeth as the rack arm is extended or retracted with respect to the cam housing such that the circular gear is rotated about the axle as the rack arm is extended or retracted. The cam is attached to the circular gear such that the cam rotates in a corresponding manner when the circular gear rotates about the axle as the rack arm is extended or retracted. The cam includes a curved cam groove having an inner end and an outer end, wherein the inner end is located radially closer to the axle than the outer end. The spring assembly includes a spring, a spring arm attached to the spring at a first end and including a follower pin at a second end of the spring arm opposite the first end, the follower pin located in the cam groove such that the spring arm moves when the cam rotates, applying a force to the spring, and a spring arm attachment also attached to the base, the tray or screen assembly, or the parallelogram arm.

The present disclosure relates to a surgical microscope assembly including a parallogram arm, a surgical microscope, an arm head, an arm base, and a movable rack assembly attached to the parallelogram arm, the arm head, or the arm base. The movable rack arm assembly includes a cam housing including an internal rack arm guide pin and an axle, a circular gear including circular gear teeth and mounted on and rotatable about the axle, a rack arm, a cam, and a spring assembly. The rack arm includes a rack arm attachment attached to the parallelogram arm, arm head, or arm base, a rack gear including rack gear teeth, and a rack arm track associated with the internal rack arm guide pin to hold the rack gear teeth engaged with the circular gear teeth as the rack arm is extended or retracted with respect to the cam housing such that the circular gear is rotated about the axle as the rack arm is extended or retracted. The cam is attached to the circular gear such that the cam rotates in a corresponding manner when the circular gear rotates about the axle as the rack arm is extended or retracted. The cam includes a curved cam groove having an inner end and an outer end, wherein the inner end is located radially closer to the axle than the outer end. The spring assembly includes a spring, a spring arm attached to the spring at a first end and including a follower pin at a second end of the spring arm opposite the first end, the follower pin located in the cam groove such that the spring arm moves when the cam rotates, applying a force to the spring, and a spring arm attachment attached to the parallelogram arm, the arm head, or the arm base.

The present disclosure relates to a customizable force profile spring assembly including a first member, a second member, a cam, and a spring. The first member is restrained, so that it can only move along a single axis. The second member is also restrained so that it can only move along a single axis. The first member is mechanically coupled to the cam, such as with a gear, so that as it travels along its axis of travel, it causes the cam to rotate. The cam, in turn, is mechanically coupled to the second member, and the rotation of the cam causes the second member to move along its axis of travel. The movement of the second member exerts force on a spring, causing the spring to deflect.

The present disclosure relates to a movable rack arm assembly including a cam housing including an internal rack arm guide pin and an axle, a circular gear including circular gear teeth and mounted on and rotatable about the axle, a rack arm, a cam, and a spring assembly. The rack arm includes a rack gear including rack gear teeth and a rack arm track associated with the internal rack arm guide pin to hold the rack gear teeth engaged with the circular gear teeth as the rack arm is extended or retracted with respect to the cam housing such that the circular gear is rotated about the axle as the rack arm is extended or retracted. The cam is attached to the circular gear such that the cam rotates in a corresponding manner when the circular gear rotates about the axle as the rack arm is extended or retracted. The cam includes a curved cam groove having an inner end and an outer end, wherein the inner end is located radially closer to the axle than the outer end. The spring assembly includes a spring and a spring arm attached to the spring at a first end and including a follower pin at a second end of the spring arm opposite the first end, the follower pin located in the cam groove such that the spring arm moves when the cam rotates, applying a force to the spring.

The above surgical console, surgical microscope assembly, customizable force profile spring assembly, or movable rack arm may each have one or more of the following additional features, which may be combined with one another or with other aspects of the present disclosure, unless clearly mutually exclusive:

i) the curved cam groove may have a radial distance from the axle that consistently increases as curved cam groove distance from the inner end increases;

ii) the curved cam groove may have a radial distance from the axle that increases and decreases as curved cam groove distance from the inner end increases;

iii) the spring may be an extension spring; and iv) the spring may be a compression spring.

BRIEF DESCRIPTION OF THE DRAWINGS

A more complete understanding of the present disclosure and its features and advantages thereof may be acquired by referring to the following description, taken in conjunction with the accompanying drawings, which are not necessarily to scale, in which like reference numbers indicate like features, and wherein.

DETAILED DESCRIPTION

The present disclosure provides a movable rack arm assembly including a movable rack arm with a counterbalance spring that allows contoured non-linear force transfer with respect to the movable rack arm. The present disclosure also provides equipment, such as surgical equipment, particularly ophthalmic surgical equipment containing such a movable rack arm assembly.

Figure 1A:
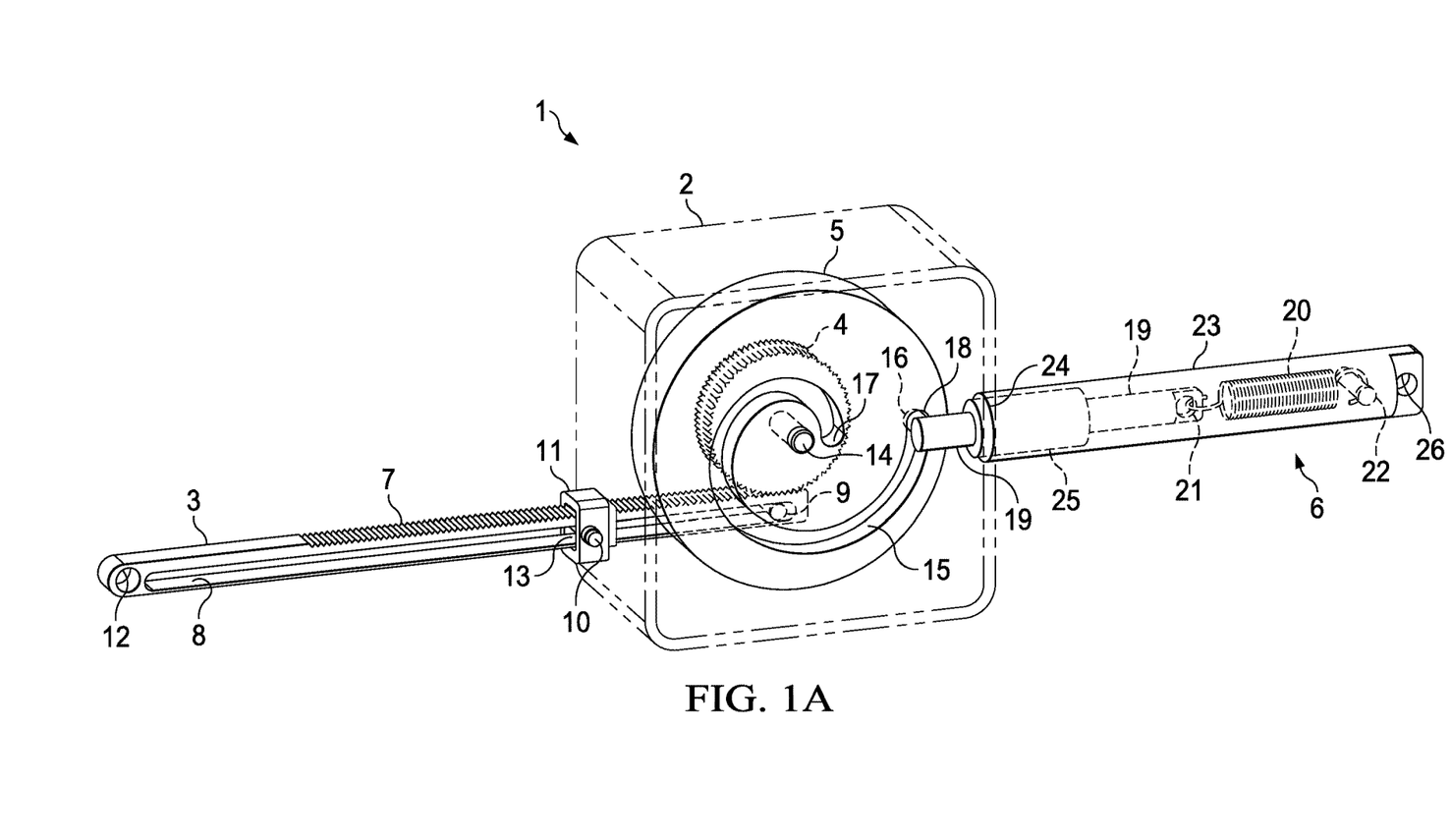
FIG. 1A is a schematic elevation view of a movable rack arm assembly with an extended movable rack arm.
Figure 1B:
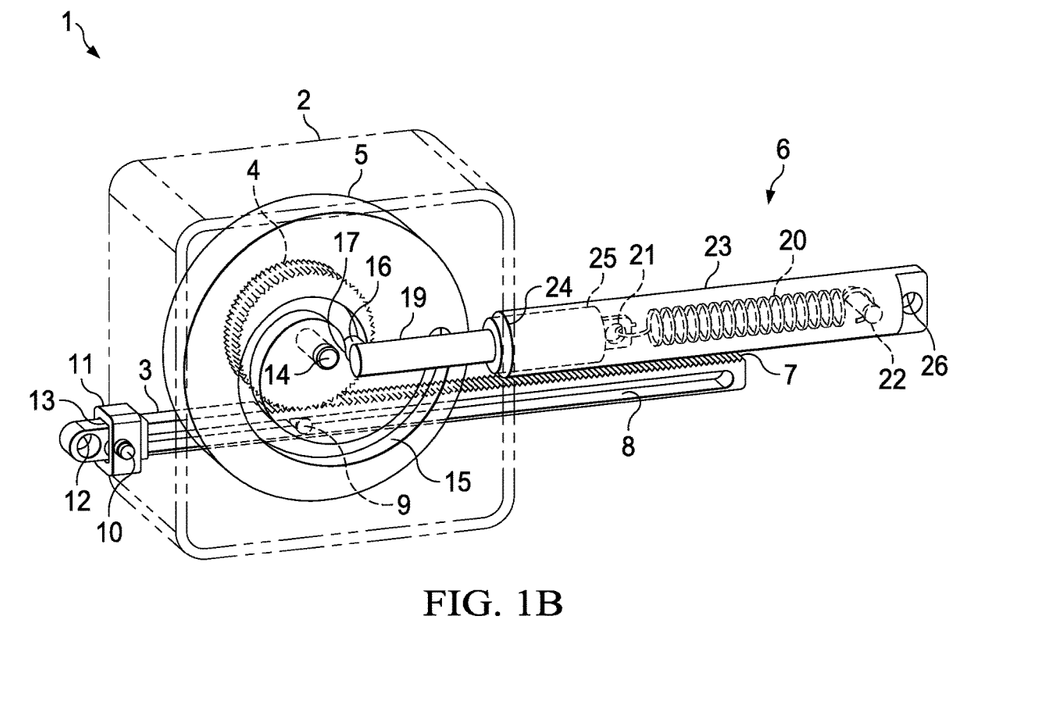
FIG. 1B is a schematic elevation view of a movable rack arm assembly of FIG. 1A, with a retracted movable rack arm.

FIG. 1A and FIG. 1B (referred to collectively as FIG. 1) illustrate a movable rack arm assembly 1, which includes cam housing 2, rack arm 3, circular gear 4, cam 5, and spring assembly 6.

Cam housing 2 may be any shape sufficient to hold attached internal rack arm guide pin 9, rack arm guide 11, and axle 14 in place with respect to one another.

Rack arm 3 includes rack gear 7 disposed on an external surface of rack arm 3. Rack arm 3 also includes rack arm track 8, which is a cavity formed wholly or partially through the interior of rack arm 3 and sized to closely fit on internal rack arm guide pin 9, which is attached to cam housing 2. Rack arm track 8 may also closely fit on rack arm guide pin 10, which is part of rack arm guide 11. Together internal rack arm guide pin 9 and housing wall rack arm guide pin 10 help keep the teeth of rack gear 7 in engaging contact with the teeth of circular gear 4 as rack arm 3 extends and retracts. Rack arm guide 11 may contain rack arm guide orifice 13 through which rack arm 3 passes as it extends and retracts. Rack arm guide orifice 13 may also help keep rack arm 3 in the proper position for the teeth of rack gear 7 to be in engaging contact with the teeth of circular gear 4 as rack arm 3 extends and retracts. Rack arm guide pin 10 may be located in rack arm guide orifice 13, as shown, or in another part of rack arm guide 11.

Rack arm 3 may also include rack arm attachment orifice 12 at an end external to cam housing 2 and opposite the end that engages with circular gear 4. Rack arm attachment orifice 12 may allow attachment to additional objects, such as further arms or components of medical equipment, such as trays, screens, microscopes, or mounting brackets.

Rack arm 3 is shown in FIG. 1 as a linear rack arm formed as one piece. However, rack arm 3 may include curved portions and may be formed as a plurality of pieces.

Circular gear 4 is mounted on axle 14 so that it may rotate around axle 14 in response to movement of rack arm 3, due to engagement of the teeth of rack gear 7 with the teeth of circular gear 4.

Circular gear 4 may be attached to cam 5, for example by adhesive, melting, screw fasteners, riveting, or welding, or circular gear 4 may be integrally formed with cam 5, as is possible in plastic injection molding or metal casting, such that rotational movement of circular gear 4 results in corresponding rotational movement of cam 5. Axle 14 may be rigidly attached to housing 2 and go through pivot holes or radial bearings mounted in cam 5 and gear 4 or both. Alternately, axle 14 may be rigidly attached to cam 5 or gear 4 or both and go through a pivot hole or bearing mounted in housing 2.

Cam 5 includes curved cam groove 15, which may be located on the same or opposite side of cam 5 as circular gear 4. Cam groove 15 may be formed wholly or partially through the interior of cam 5. Curved cam groove 15 is sized to closely fit follower pin 16, so that follower pin 16 may move along curved cam groove 15, but will engage the walls of curved cam groove 15 with sufficient static friction to remain in place, even when a force is exerted by spring 20, throughout the entire extension or retraction of rack arm 3 as permitted by the length of rack arm track 8.

Curved cam groove 15 has an inner end 17 and an outer end 18. Inner end 17 is a shorter radial distance from axle 14 than outer end 18. The increase in radial distance from axle 14 as a function of curved cam groove 15 distance from inner end 17 may vary. In addition, although FIG. 1 shows a curved cam groove 15 for which the radial distance from axle 14 consistently increases as curved cam groove 15 distance from inner end 17 increases, other groove configurations are possible, such as those in which radial distance from axle 14 increases and decreases as curved cam groove 15 distance from inner end 17 increases. Such a curved cam groove 15 would exhibit a wave shape.

As cam 5 rotates in response to a force applied to rack arm 3, follower pin 16 moves in cam groove 15. Follower pin 16 is part of spring arm 19 in spring assembly 6, so spring arm 19 also moves. Follower pin 16 may include a radial ball bearing (not shown) to allow lower friction contact with the cam groove 15. Movement of spring arm 19 is resisted by spring 20, which is attached to spring arm 19, for example by spring attachment hole 21, and to spring cam housing 23, for example by spring attachment pin 22, which is attached to spring cam housing 23.

Spring arm 19 is able to move in and out of cam housing 2 through spring arm orifice 24. Spring arm 19 may be held in place by spring arm guide 25, through which spring arm 19 passes. Spring arm guide 25 may be located, at one end, in spring arm orifice 24, or if may be securely held in spring housing 23, or both. Spring housing 23 may also be attached to cam housing 2 around spring arm orifice 24.

Spring assembly 6, and particularly spring housing 23, may also include spring arm attachment orifice 26 at an end external to cam housing 2 and opposite follower pin 19. Spring arm attachment orifice 26 may allow attachment to additional objects, such as mounting brackets and chassis.

Spring 20 as shown is an extension spring, which resists forces that axially lengthen spring 20. Spring 20 may also be a compression spring, which resists forces that axially shorten spring 20. Other spring formats may also be used.

In FIG. 1A, rack arm 3 is in a fully extended position. In FIG. 1B, rack arm 3 is in a fully retracted position. It will be understood that, during use of movable rack arm assembly 1, rack arm 3 may move between the fully extended position and the fully retracted position, which may also result in movement of circular gear 4 and cam 5, such that follower pin 16 will be in a different position along curved cam groove 15 than is shown in FIG. 1A or FIG. 1B and spring 20 will be differently extended or compressed.

Figure 2:
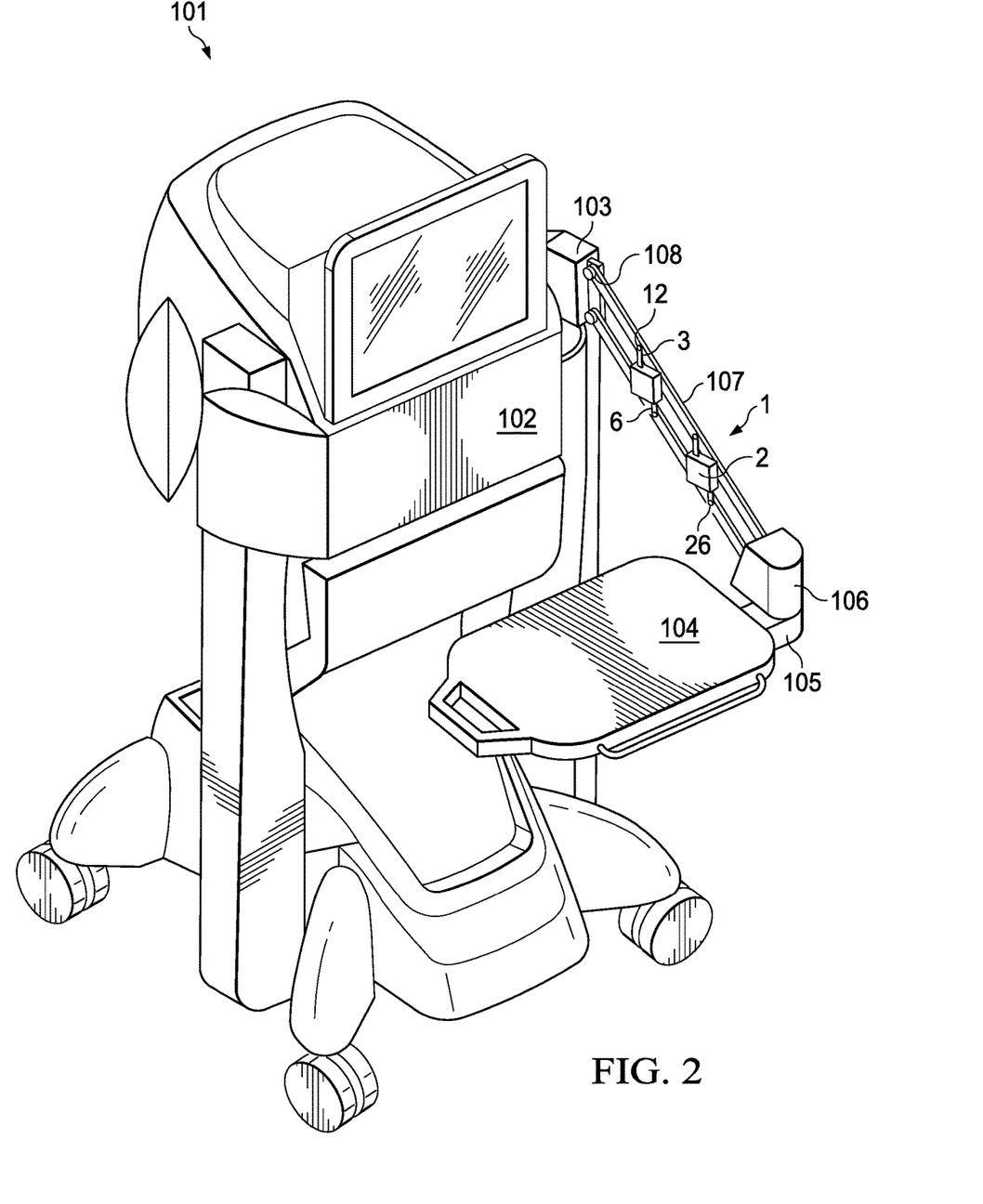
FIG. 2 is a schematic elevation view of a surgical console including surgical tray having a movable rack arm assembly of FIG. 1A and FIG. 1B.

As illustrated in FIG. 2, movable rack arm assembly 1 may be part of a surgical console 101. Surgical console 101 includes base 102 to which mounting attachment 103 is attached. Parallelogram arm 107 connects mounting attachment 103 to tray joint 106 and attaches at arm joints 108. Arm joints 108 may operate, for example as shown using a screw, bolt, or shaft. Arm joints 108 may also operate using other mechanisms, such as flanges, slots, or snap joints. Movable rack arm assembly 1 may be mounted to parallelogram arm 107 using rack arm 3 and/or spring assembly 6. Rack arm 3 and/or spring assembly 6 may be attached to parallelogram arm 107, for example as shown using a screw, bolt, or shaft placed through rack arm attachment orifice 12 and/or spring assembly attachment orifice 26. Rack arm 3 and spring assembly 6 may be attached directly to base 102 or mounting attachment 103 in a similar manner. In addition, rack arm 3 and spring assembly 6 may be attached to parallelogram arm 107, mounting attachment 103, or directly to base 102 using other mounting mechanisms, such as flanges and slots or snap joints.

Surgical console 101 also includes tray 104 which may be attached to parallelogram arm 107, for example at arm joints 108. As illustrated, tray 104 is attached to tray arm 105 which is attached to tray joint 106. FIG. 2 also shows tray joint 106 connected to mounting attachment 103 by parallelogram arm 107. However, tray arm 105, tray joint 106, or tray 104 may be attached directly to rack arm 3, spring assembly 6, and/or parallelogram arm 107.

Although surgical console 101 is depicted with tray 104, other objects, such as a screen, may be mounted in a manner similar to and used in place of tray 104.

In addition, although FIG. 2 depicts attachment of tray 104 or similar object to base 102 to form surgical console 101, a wall or bed mount may be used in place of base 102.

Figure 3A:
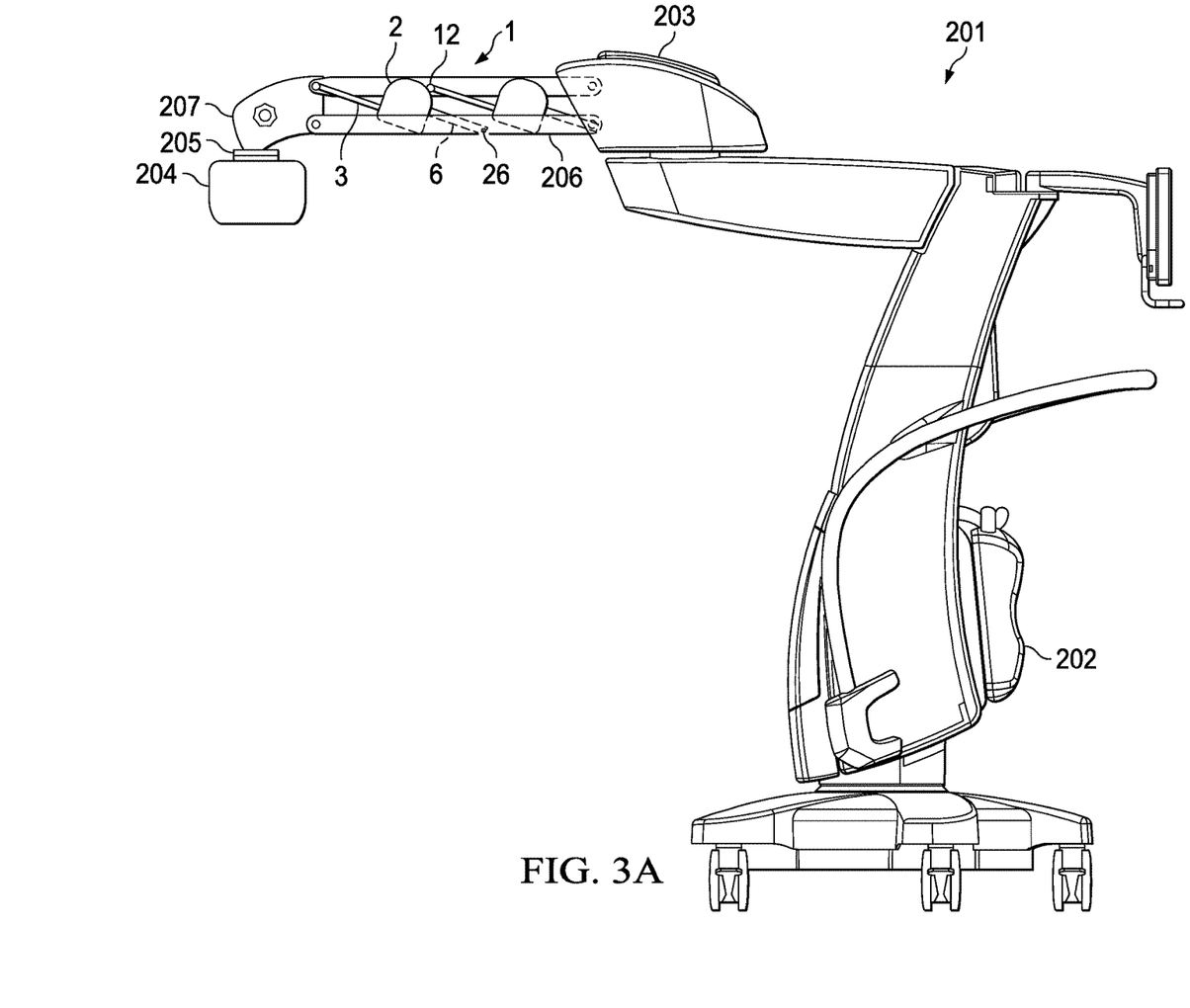
FIG. 3A is a schematic elevation view of a surgical ophthalmic microscope having a movable rack arm assembly of FIG. 1A and FIG. 1B.

As illustrated in FIG. 3A, movable rack arm assembly 1 may be part of a surgical microscope system 201. Surgical microscope system 201 includes base 202 to which arm body 203 is attached. Arm body 203 may be attached to microscope mount 205 via parallelogram arm 206 and arm head 207. Arm body 203 is the point of attachment for parallelogram arm 206. Arm body 203 may be part of base 202. Movable rack arm assembly 1 may be mounted to parallelogram arm 206, for example as shown using a screw, bolt, or shaft placed through spring assembly attachment orifice 26 and rack arm attachment orifice 12. Spring assembly 6 and rack arm 3 may also be attached to parallelogram arm 206 using other mounting mechanisms, such as flanges and slots or snap joints.

Surgical microscope system 201 also includes surgical microscope 204, which may be an ophthalmic surgical microscope. Surgical microscope 204 may be attached to microscope mount 205. Surgical microscope 204, arm head 207, or arm body 203 may be attached directly to rack arm 3 or spring assembly 6 through a screw, bolt, or shaft placed through rack arm attachment orifice 12 or spring assembly attachment orifice 26. In addition, rack arm 3 and spring assembly 6 may be attached using other mounting mechanisms, such as flanges, slots, or snap joints.

Although surgical microscope system 201 is depicted with surgical microscope 204, other objects, particularly other measurement equipment, such as an OCT scanner, may be mounted in a manner similar to and used in place of surgical microscope 204.

In addition, although FIG. 3A depicts attachment of arm body 203 to base 202 a wall or bed mount may be used in place of base 202. Furthermore, parallelogram arm 207 might be attached to base 202, or may also be attached to a wall or bed mount.

In use, movement of follower pin 16 along curved cam groove 15 in response to extension or retraction of rack arm 3 causes a non-linear transfer of force, due to compression or extension of spring 20. As a result, a different amount of force is needed to extend to retract rack arm 3, depending on how far it is already extended or retracted.

Figure 3B:
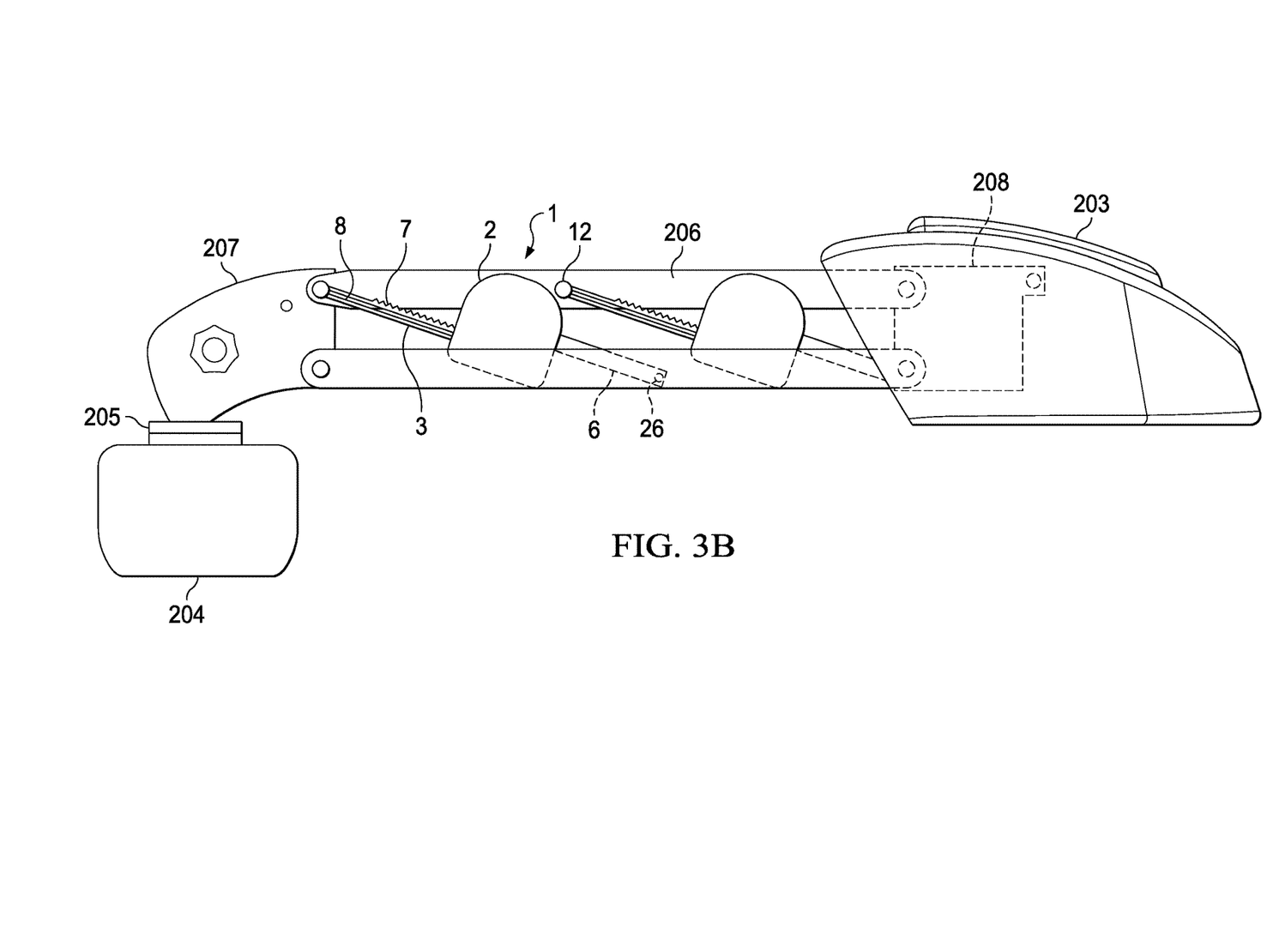
FIG. 3B is a schematic elevation view of a surgical ophthalmic microscope arm having a movable rack arm assembly of FIG. 1A and FIG. 1B in the middle position.

FIG. 3B shows a magnified view of FIG. 3A with the parallelogram arm 206 in the middle position.

Figure 3C:
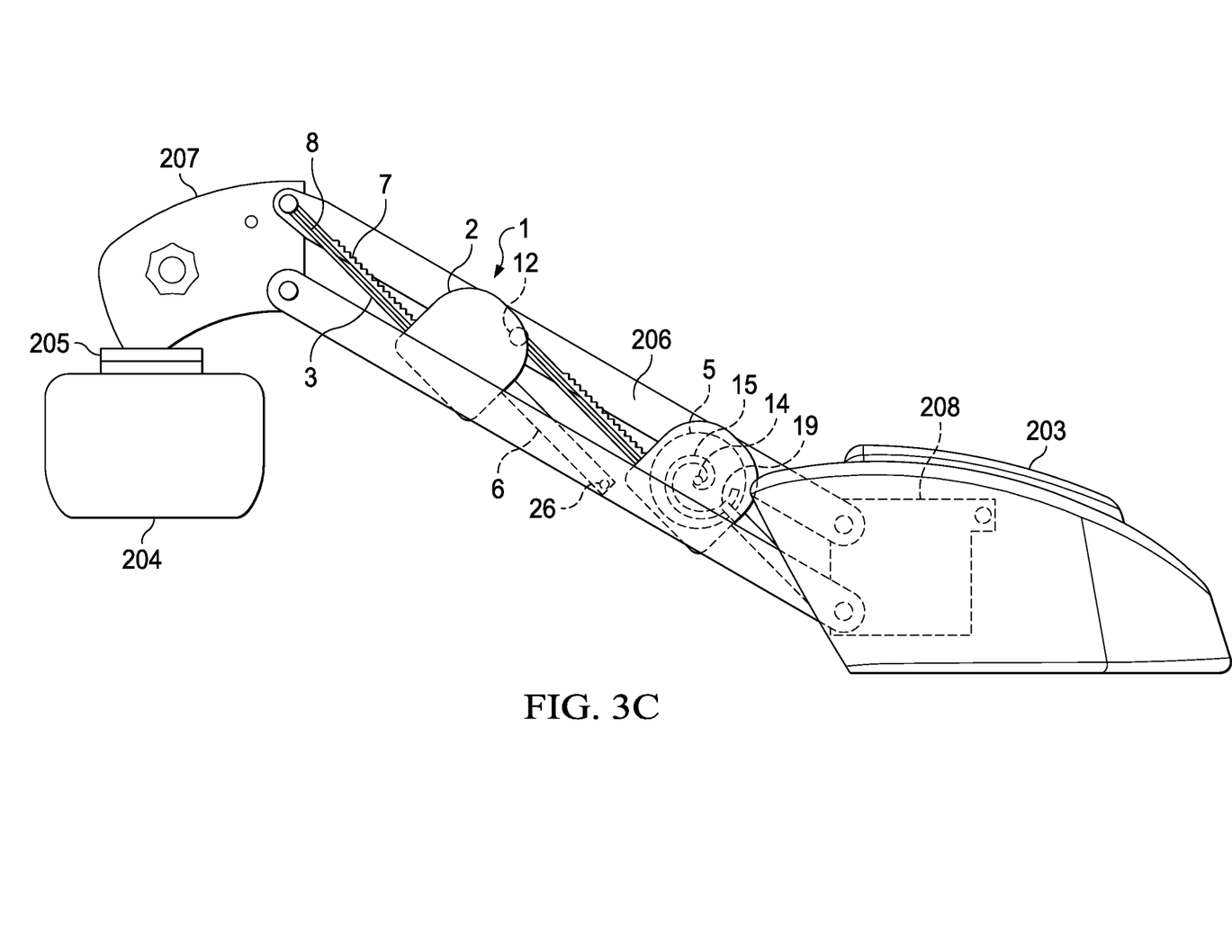
FIG. 3C is a schematic elevation view of a surgical ophthalmic microscope arm having a movable rack arm assembly of FIG. 1A and FIG. 1B in the up position.

FIG. 3C shows a magnified view of FIG. 3A with the parallelogram arm 206 in the end-of-travel up position. Even when the parallelogram arm 206 is at end-of-travel, the follower pin 16 might not be at the end of the curved cam groove 15. Therefore, the range of operation allowed by the mechanism may be more than the parallelogram arm requires.

Figure 3D:
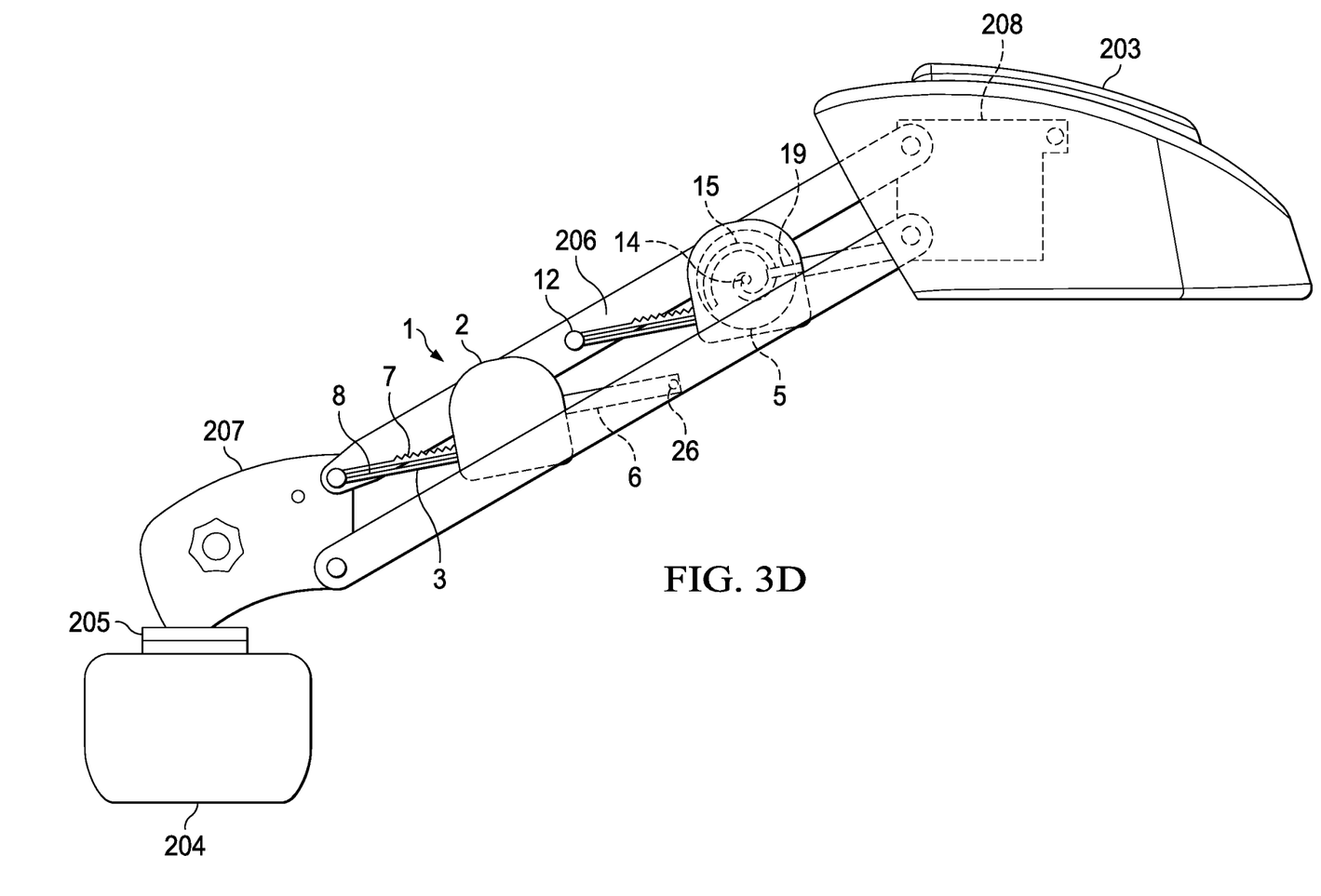
FIG. 3D is a schematic elevation view of a surgical ophthalmic microscope arm having a movable rack arm assembly of FIG. 1A and FIG. 1B in the down position.

FIG. 3D shows a magnified view of FIG. 3A with the parallelogram arm 206 in the end-of-travel down position. Even when the parallelogram arm 206 is at end-of-travel, the follower pin 16 might not be at the end of the curved cam groove 15. Therefore, the range of operation allowed by the mechanism may be more than the parallelogram arm requires.

Figure 4:
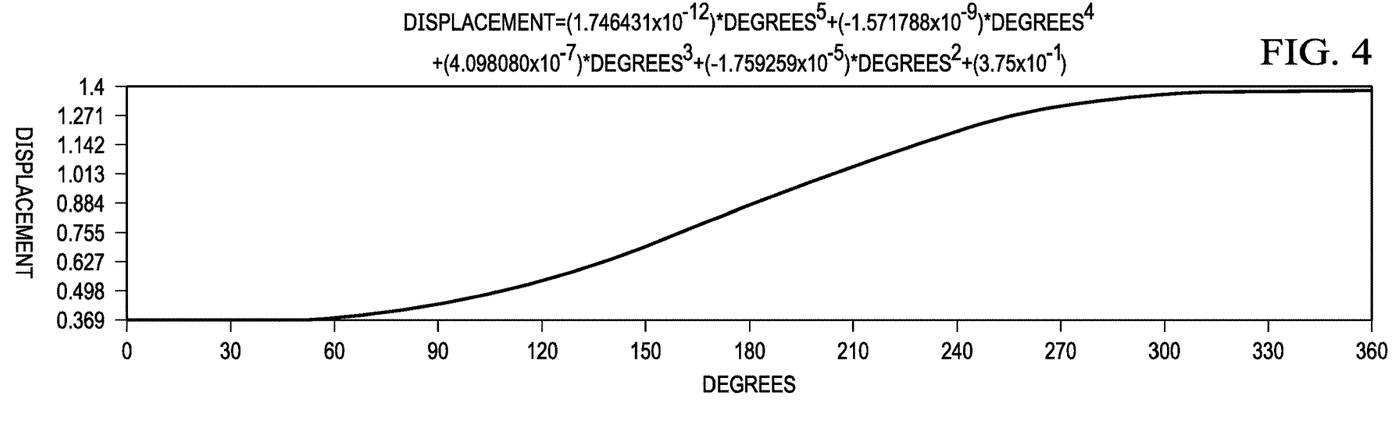
FIG. 4 is a graph showing displacement of a rack arm as a function of degrees of rotation of a cam in the movable rack arm assembly of FIG. 1A and FIG. 1B.

FIG. 4 is a representative graph generated using a fifth order polynomial illustrating the displacement of rack arm 3 as a function of degrees of rotation of cam 5.

Figure 5:
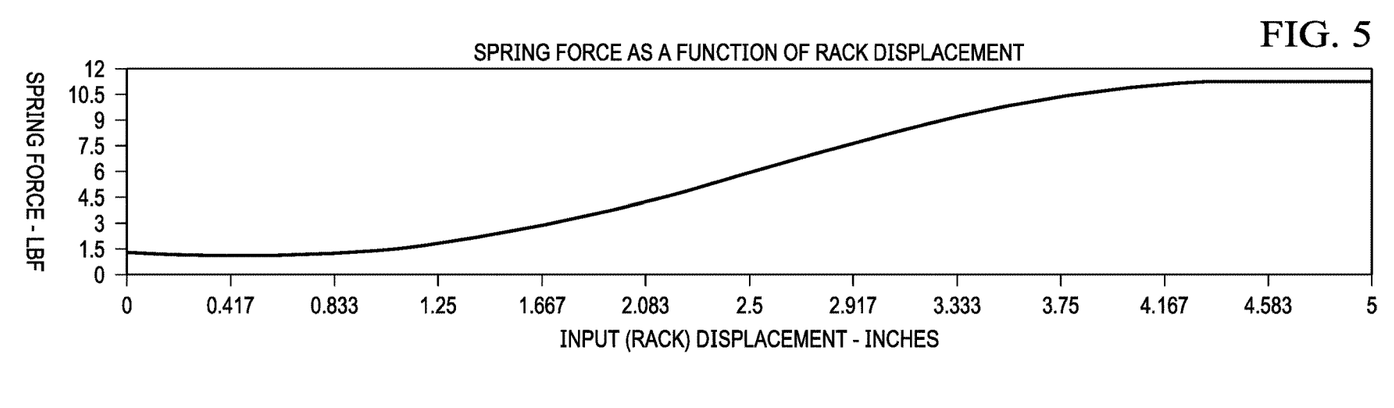
FIG. 5 is a graph showing spring force of an extension counterbalance spring as a function of displacement of a rack arm in the movable rack arm assembly of FIG. 1A and FIG. 1B.

FIG. 5 is a representative graph of the spring force of an extension counterbalance spring 20 as a function of displacement of rack arm 3. As illustrated, the spring force does not linearly correspond with rack arm 3 displacement because rack arm 3 displacement does not result in a linear increase in extension of spring 20. Instead, extension of spring 20 is modulated by rotation of cam 5 and movement of follower pin 16 in curved cam groove 15.

Figure 6:
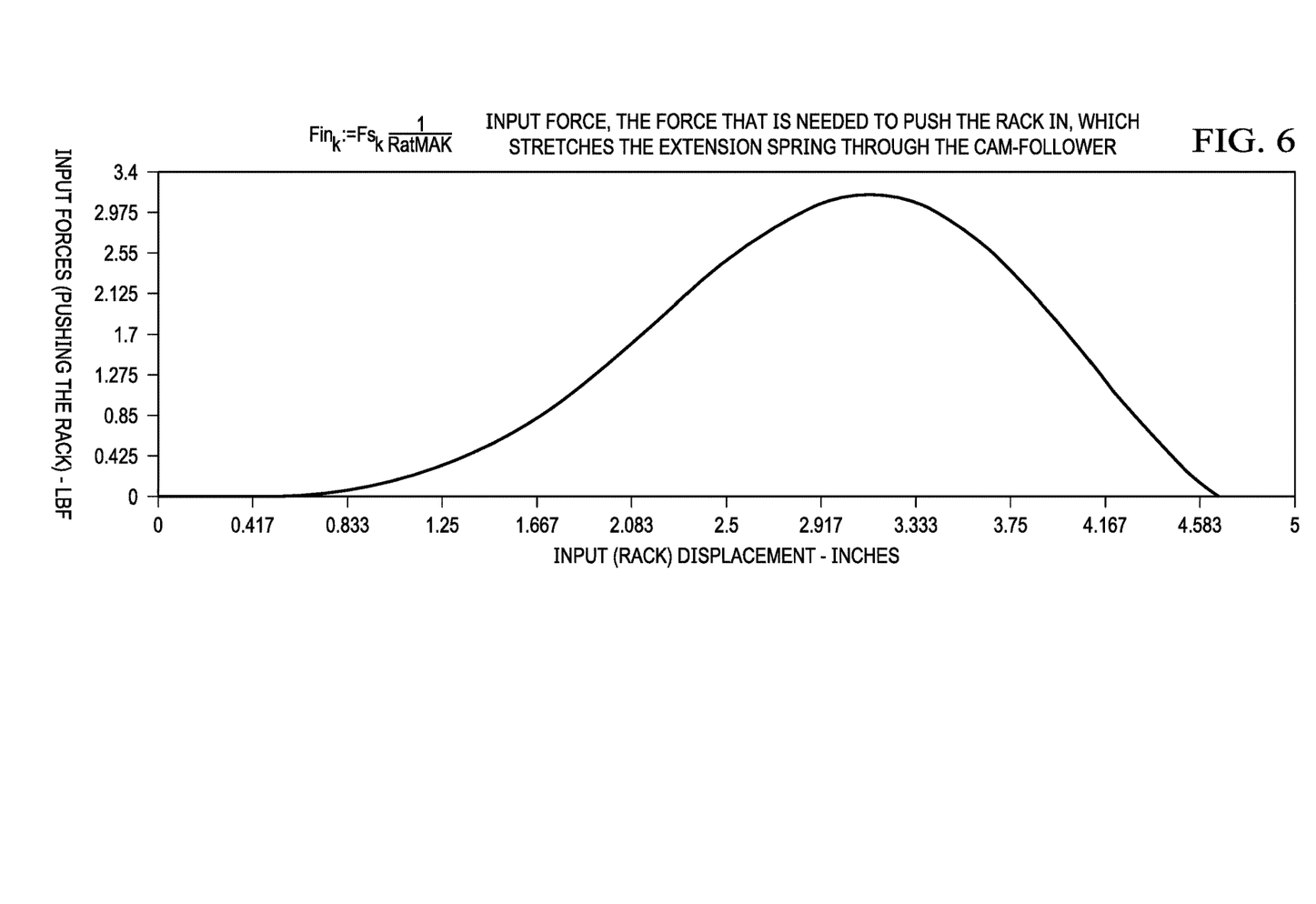
FIG. 6 is a graph showing user input force, which can also be characterized as the counterbalance force, as a function of displacement of a rack arm in the movable rack arm assembly of FIG. 1A and FIG. 1B.

FIG. 6 is a representative graph showing user input force as a function of displacement of rack arm 3 in the same system of FIG. 5. As FIG. 6 makes clear, the amount of force needed to cause further displacement of rack arm 3 is not constant. Instead, it increases to a point, then decreases, due to rotation of cam 5.

A movable rack arm assembly 1 exhibiting a user force to displacement profile as shown in FIG. 6 would be useful for a situation in which accidental bumping is a concern. An accidental bump would be unlikely to be enough to cause rack arm 3 to move very much. However, rack arm 3 could be intentionally moved by exerting sufficient force, then have its position finely tuned using minimal force one rack arm 3 extension reached a certain distance.

Other force profiles may be generated as well. For example, if cam 5 had a wave-shaped curved inner groove 5, then the user force to displacement profile might exhibit two hills with a valley between them. Such as profile might be useful when an intermediate displacement of rack arm 3 is desired and fine adjustments are needed only at those displacement lengths.

Movable rack arm assembly 1 may also reduce acceleration of arm movement and jerking movements of the arm.

The force needed to cause movement of rack arm 3 may vary depending on the use of movable rack arm assembly 1, but typically a force of between 2 and 20, between 2 and 10, or between 2 and 4, inclusive, may be used for surgical equipment. Typically a force of between 8 and 12, inclusive and particularly around 10 lbf may be used for surgical trays, such as tray 104 and similar objects. Typically a force of between 2 and 4, inclusive lbf may be used for surgical microscopes, such as surgical microscope 204 and similar objects.

Although the above description uses a single movable arm 1 to illustrate the principles of the disclosure, multiple movable rack arm assemblies 1, with the same or different types of springs and the same or different spring constants may be combined to generate more complex user force to displacement profiles.

Figure 7A:
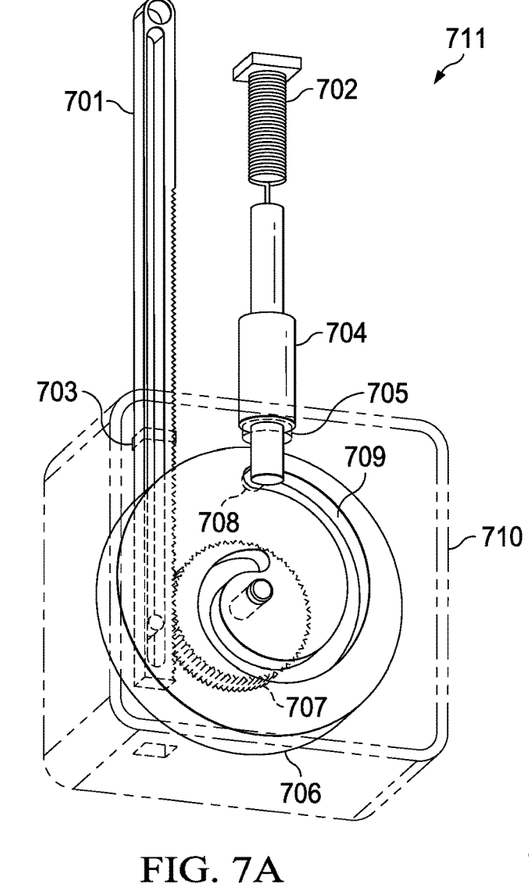
FIG. 7A is a schematic elevation view of a first embodiment of a customizable force profile spring assembly with an extended first member.
Figure 7B:
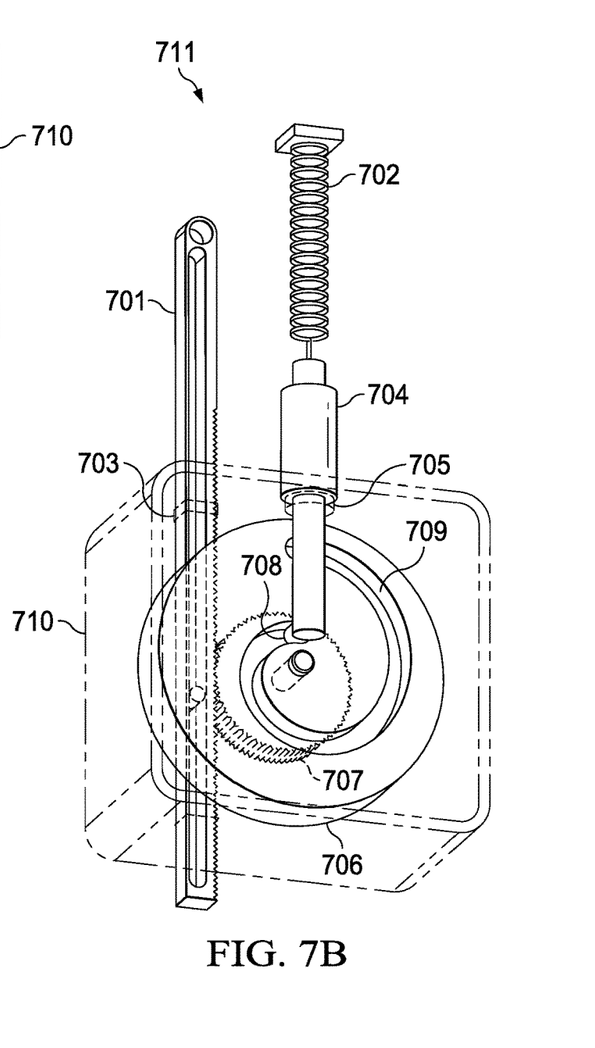
FIG. 7B is a schematic elevation view of a first embodiment of a customizable force profile spring assembly with a retracted first member.

FIG. 7A and FIG. 7B (referred to collectively as FIG. 7) illustrate a first embodiment of customizable force profile spring assembly 711, which includes a first member 701, a second member 704, a cam 706, a gear 707, and a housing 710.

The housing 710 acts as an anchor to hold first restraint 703 and second restraint 705 in place relative to the other components of the customizable force profile spring assembly 711.

First restraint 703 and second restraint 705 are aperture walls which only allow first member 701 and second member 704 to extend and retract. First restraint 703 keeps first member 701 engaged with gear 707 during extension and retraction. Gear 707 is connected to cam 706, so that when first member 701 extends or retracts, cam 706 turns.

In this embodiment, cam 706 is mechanically coupled to second member 704 through pin 708. Pin 708 slots into curved groove 709, so that when cam 706 rotates, pin 708 slides along curved groove 709. Because curved groove 709 is curved toward the center of gear 708, pin 708 pulls second member 704 toward the center of gear 708 as cam 706 rotates.

In FIG. 7, second member 704 is attached directly to spring 702, such that when second member 704 is pulled toward the center of gear 708, spring 702 is deflected. Spring 702's deflection may increase or decrease the force required to extend or retract first member 701.

FIG. 7A shows first member 701 fully extended. In this embodiment, when first member 701 is fully extended spring 702 is compressed and pin 708 is at the outermost end of curved groove 709. However, in other embodiments, extending first member 701 might extend spring 702, or pin 708 might be at another point in curved groove 709.

FIG. 7B shows first member 701 fully retracted. In this embodiment, when first member 701 is fully retracted, spring 702 is extended and pin 708 is at the innermost end of curved groove 709. However, in other embodiments, retracting first member 701 might retract spring 702, or pin 708 might be at another point in curved groove 709. In other embodiments, the curved groove 709 may have a different curvature, which will generate a different force profile.

Figures 8A, 8B:
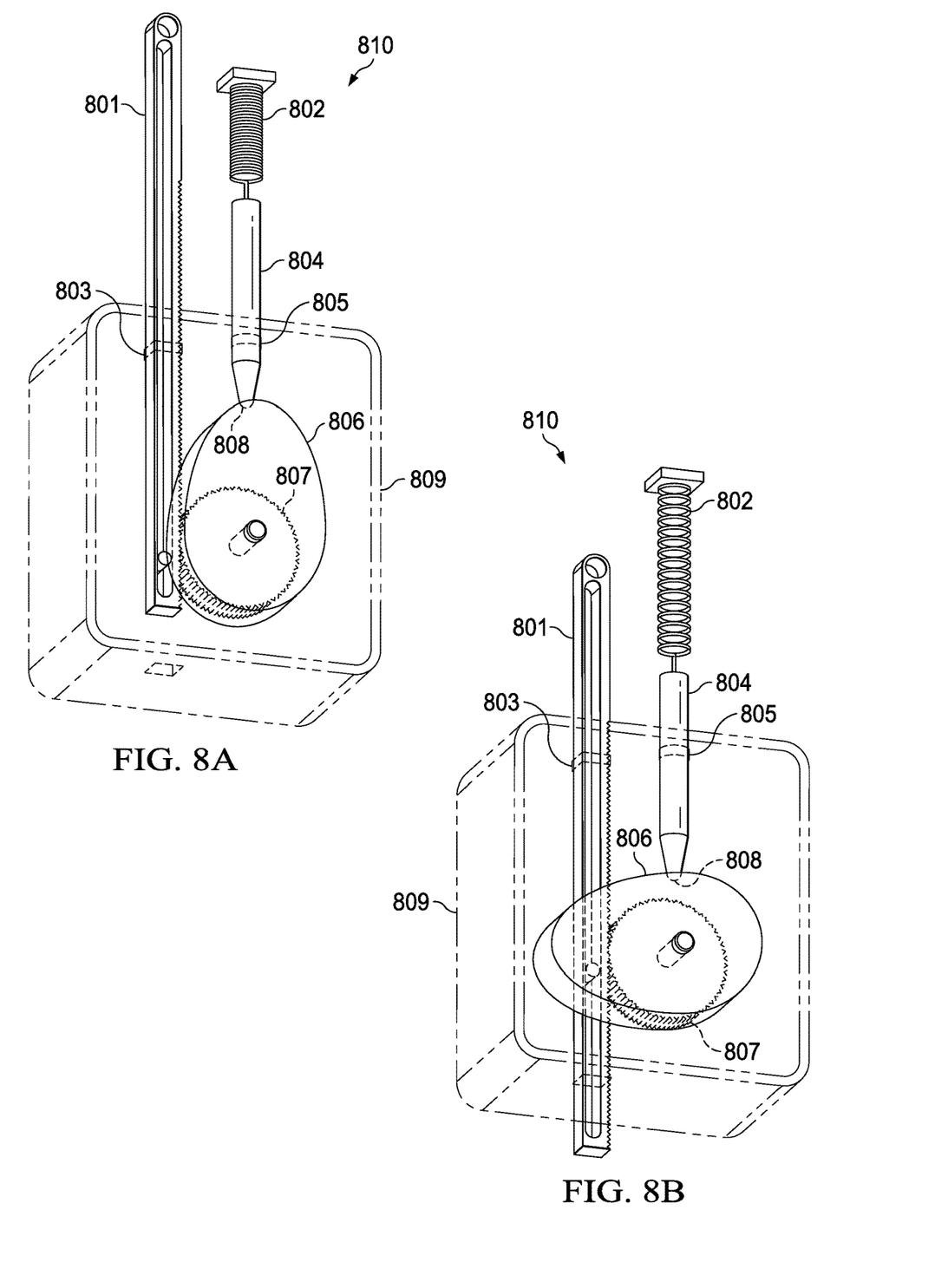
FIG. 8A is a schematic elevation view of a second embodiment of customizable force profile spring assembly with an extended first member.
FIG. 8B is a schematic elevation view of a second embodiment of customizable force profile spring assembly with a retracted first member.

FIG. 8A and FIG. 8B (referred to collectively as FIG. 8) illustrate a second embodiment of customizable force profile spring assembly 810, which includes a first member 801, a second member 804, a cam 806, a gear 807, and a housing 809.

The housing 809 acts as an anchor to hold first restraint 803 and second restraint 805 in place relative to the other components of the customizable force profile spring assembly 810.

First restraint 803 and second restraint 805 are aperture walls which only allow first member 801 and second member 804 to extend and retract. First restraint 803 keeps first member 801 engaged with gear 807 during extension and retraction. Gear 807 is connected to cam 806, so that when first member 801 extends or retracts, cam 806 turns.

In this embodiment, cam 806 is mechanically coupled to second member 804 through cam follower 808. Cam follower 808 is depicted as a needle bearing, but could be a roller bearing or any other type of cam follower. The oblong shape of cam 806 causes cam follower 808 to push against second member 804 as cam 806 rotates. Cam 806 may be in different shapes, and different shapes will create different force profiles.

In FIG. 8, second member 804 is attached directly to spring 802, such that when second member 804 is pulled toward the center of gear 808, spring 802 is deflected. Spring 802's deflection may increase or decrease the force required to extend or retract first member 801.

FIG. 8A shows first member 801 fully extended. In this embodiment, when first member 801 is fully extended spring 802 is compressed and cam 806 pushes cam follower 808 to its furthest extent. However, in other embodiments, extending first member 801 might position cam 806 in another orientation; for example, such that cam follower 808 is at its innermost extent.

FIG. 8B shows first member 802 fully retracted. In this embodiment, when first member 801 is fully retracted spring 802 is extended and cam follower 808 is at its innermost extent. However, in other embodiments, extending first member 801 might position cam 806 in another orientation; for example, such that cam follower 808 is at its outermost extent.

Although the present disclosure and its advantages have been described in detail, it should be understood that various changes, substitutions and alternations can be made herein without departing from the spirit and scope of the disclosure as defined by the following claims.

The invention claimed is:

1. A surgical console comprising:
   a base;
   a tray assembly;
   a parallelogram arm comprising a first bar and a second bar; and
   a movable rack arm assembly attached to at least one bar of the parallelogram arm, the movable rack arm assembly comprising:
      a cam housing comprising an internal rack arm guide pin and an axle;
      a circular gear comprising circular gear teeth and mounted on and rotatable about the axle;
      a rack arm comprising:
         a rack arm attachment attached to a bar of the parallelogram arm;
         a rack gear comprising rack gear teeth; and
         a rack arm track associated with the internal rack arm guide pin to hold the rack gear teeth engaged with the circular gear teeth as the rack arm is extended or retracted with respect to the cam housing such that the circular gear is rotated about the axle as the rack arm is extended or retracted;
      a cam attached to the circular gear such that the cam rotates in a corresponding manner when the circular gear rotates about the axle as the rack arm is extended or retracted, the cam comprising a curved cam groove having an inner end and an outer end, wherein the inner end is located radially closer to the axle than the outer end; and
      a spring assembly comprising:
         a spring;
         a spring arm attached to the spring at a first end and comprising a follower pin at a second end of the spring arm opposite the first end, the follower pin located in the cam groove such that the spring arm moves when the cam rotates, applying a force to the spring; and
         a spring arm attachment attached to the parallelogram arm.

2. The surgical console of claim 1, wherein the curved cam groove has a radial distance from the axle that consistently increases as curved cam groove distance from the inner end increases.

3. The surgical console of claim 1, wherein the curved cam groove has a radial distance from the axle that increases and decreases as curved cam groove distance from the inner end increases.

4. The surgical console of claim 1, wherein the spring is an extension spring.

5. The surgical console of claim 1, wherein the spring is a compression spring.

6. A surgical microscope assembly comprising:
   a parallelogram arm comprising a first bar and a second bar;
   an arm body;
   an arm head;
   a surgical microscope; and
   a movable rack arm assembly attached to at least one bar of the parallelogram arm, the movable rack arm assembly comprising:
      a cam housing comprising an internal rack arm guide pin and an axle;
      a circular gear comprising circular gear teeth and mounted on and rotatable about the axle;
      a rack arm comprising:
         a rack arm attachment attached to the arm head, the parallelogram arm;
         a rack gear comprising rack gear teeth; and
         a rack arm track associated with the internal rack arm guide pin to hold the rack gear teeth engaged with the circular gear teeth as the rack arm is extended or retracted with respect to the cam housing such that the circular gear is rotated about the axle as the rack arm is extended or retracted;
      a cam attached to the circular gear such that the cam rotates in a corresponding manner when the circular gear rotates about the axle as the rack arm is extended or retracted, the cam comprising a curved cam groove having an inner end and an outer end, wherein the inner end is located radially closer to the axle than the outer end; and
      a spring assembly comprising:
         a spring;
         a spring arm attached to the spring at a first end and comprising a follower pin at a second end of the spring arm opposite the first end, the follower pin located in the cam groove such that the spring arm moves when the cam rotates, applying a force to the spring; and
         a spring arm attachment attached to the parallelogram arm.

7. The surgical microscope assembly of claim 6, wherein the curved cam groove has a radial distance from the axle that consistently increases as curved cam groove distance from the inner end increases.

8. The surgical microscope assembly of claim 6, wherein the curved cam groove has a radial distance from the axle that increases and decreases as curved cam groove distance from the inner end increases.

9. The surgical microscope assembly of claim 6, wherein the spring is an extension spring.

10. The surgical microscope of claim 6, wherein the spring is a compression spring.

* * * * *